(12) United States Patent
Martin et al.

(10) Patent No.: US 10,849,629 B2
(45) Date of Patent: Dec. 1, 2020

(54) MEDICAL BALLOON

(71) Applicant: BOSTON SCIENTIFIC SCIMED, INC., Maple Grove, MN (US)

(72) Inventors: Daryl Lee Martin, Plymouth, MN (US); Jeffrey S. Lindquist, Maple Grove, MN (US); Daniel James Horn, Shoreview, MN (US); Pieter Spitael, New Brighton, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 204 days.

(21) Appl. No.: 15/839,416

(22) Filed: Dec. 12, 2017

(65) Prior Publication Data

US 2018/0161040 A1 Jun. 14, 2018

Related U.S. Application Data

(60) Provisional application No. 62/433,730, filed on Dec. 13, 2016.

(51) Int. Cl.
*A61B 17/12* (2006.01)
*A61M 25/10* (2013.01)
(Continued)

(52) U.S. Cl.
CPC .. *A61B 17/12136* (2013.01); *A61B 17/12027* (2013.01); *A61L 29/06* (2013.01); *A61M 25/10* (2013.01); *A61M 25/104* (2013.01); *A61M 25/1029* (2013.01); *A61B 2017/00831* (2013.01); *A61F 2/82* (2013.01);
(Continued)

(58) Field of Classification Search
CPC .......... A61M 25/10; A61M 2025/1031; A61M 2025/1075; A61M 25/0043; A61M 25/1029; A61M 25/104; A61B 17/12027; A61B 17/12136; A61B 2017/00831;
(Continued)

(56) References Cited

U.S. PATENT DOCUMENTS 3,023,982 A 3/1962 Huch
4,327,736 A 5/1982 Inoue
(Continued)

FOREIGN PATENT DOCUMENTS

EP 0553960 A1 1/1993
EP 0540858 A1 5/1993
(Continued)

OTHER PUBLICATIONS

International Search Report and Written Opinion dated Jun. 28, 2017 for International Application No. PCT/US2017/027032.
(Continued)

*Primary Examiner* — Yan Lan
(74) *Attorney, Agent, or Firm* — Seager, Tufte & Wickhem LLP.

(57) ABSTRACT

Composite expandable medical balloons and methods for forming composite expandable medical balloons are disclosed. An example composite expandable medical balloon may include a base balloon. A fiber braid may be disposed along the base balloon. The base balloon may have a first length prior to heat sterilization of the composite expandable medical balloon, and a second length after heat sterilization of the composite expandable medical balloon. The second length may be at least 95% of the first length.

13 Claims, 10 Drawing Sheets (51) Int. Cl.
*A61L 29/06* (2006.01)
*A61F 2/82* (2013.01)
*A61B 17/00* (2006.01)
*A61M 25/00* (2006.01)

(52) U.S. Cl.
CPC ...... *A61L 2420/08* (2013.01); *A61M 25/0043* (2013.01); *A61M 2025/1031* (2013.01); *A61M 2025/1075* (2013.01)

(58) Field of Classification Search
CPC ...... A61L 29/06; A61L 2420/08; C08L 75/04; C08L 77/00; A61F 2/82
See application file for complete search history.

(56) References Cited

U.S. PATENT DOCUMENTS

| | | | |
|---|---|---|---|
| 4,490,421 A | 12/1984 | Levy | |
| 4,706,670 A | 11/1987 | Andersen et al. | |
| 4,808,465 A | 2/1989 | Vane | |
| 4,896,669 A | 1/1990 | Bhate et al. | |
| 4,906,244 A | 3/1990 | Pinchuk et al. | |
| 4,935,190 A | 6/1990 | Tennerstedt | |
| 4,950,239 A | 8/1990 | Gahara et al. | |
| 4,963,313 A | 10/1990 | Noddin et al. | |
| 5,026,607 A | 6/1991 | Kiezulas | |
| 5,096,848 A | 3/1992 | Kawamura | |
| 5,135,516 A | 8/1992 | Sahatjian et al. | |
| 5,201,706 A | 4/1993 | Noguchi et al. | |
| 5,250,069 A | 10/1993 | Nobuyoshi et al. | |
| 5,264,260 A | 11/1993 | Saab | |
| 5,270,086 A | 12/1993 | Hamlin | |
| 5,304,121 A | 4/1994 | Sahatjian | |
| 5,304,340 A | 4/1994 | Downey | |
| 5,306,246 A | 4/1994 | Sahatjian et al. | |
| 5,314,443 A | 5/1994 | Rudnick | |
| 5,328,468 A | 7/1994 | Kaneko et al. | |
| 5,330,428 A | 7/1994 | Wang et al. | |
| 5,330,429 A | 7/1994 | Noguchi et al. | |
| 5,344,400 A | 9/1994 | Kaneko et al. | |
| 5,403,340 A | 4/1995 | Wang et al. | |
| 5,407,623 A | 4/1995 | Zachariades et al. | |
| 5,500,180 A | 3/1996 | Anderson et al. | |
| 5,503,631 A | 4/1996 | Onishi et al. | |
| 5,509,899 A | 9/1996 | Fan et al. | |
| 5,556,383 A | 9/1996 | Wang et al. | |
| 5,576,072 A | 11/1996 | Hostettler et al. | |
| 5,578,374 A | 11/1996 | Dunbar et al. | |
| 5,647,848 A | 7/1997 | Jorgensen | |
| 5,693,034 A | 12/1997 | Buscemi et al. | |
| 5,702,756 A | 12/1997 | McKean et al. | |
| 5,714,110 A | 2/1998 | Wang et al. | |
| 5,797,877 A | 8/1998 | Hamilton et al. | |
| 5,827,289 A | 10/1998 | Reiley et al. | |
| 5,833,657 A | 11/1998 | Reinhardt et al. | |
| 5,868,708 A | 2/1999 | Hart et al. | |
| 5,913,861 A | 6/1999 | Trotta | |
| 5,958,582 A | 9/1999 | Dunbar et al. | |
| 6,110,483 A | 8/2000 | Whitbourne et al. | |
| 6,146,356 A | 11/2000 | Wang et al. | |
| 6,156,254 A | 12/2000 | Andrews et al. | |
| 6,267,775 B1 | 7/2001 | Clerc et al. | |
| 6,270,522 B1 | 8/2001 | Simhambhatla et al. | |
| 6,306,144 B1 | 10/2001 | Sydney et al. | |
| 6,416,494 B1 | 7/2002 | Wilkins | |
| 6,444,324 B1 | 9/2002 | Yang et al. | |
| 6,528,150 B2 | 3/2003 | Nazarova et al. | |
| 6,572,813 B1 | 6/2003 | Zhang et al. | |
| 6,673,053 B2 | 1/2004 | Wang et al. | |
| 6,695,809 B1 | 2/2004 | Lee | |
| 6,723,267 B2 | 4/2004 | Simmelink et al. | |
| 6,746,425 B1 | 6/2004 | Beckham | |
| 6,896,892 B2 | 5/2005 | Mount et al. | |
| 7,252,650 B1 | 8/2007 | Andrews et al. | |
| 7,635,510 B2 | 12/2009 | Horn et al. | |
| 2003/0054090 A1 | 3/2003 | Hansen | |
| 2003/0106346 A1 | 6/2003 | Matsumoto | |
| 2003/0139798 A1 | 7/2003 | Brown et al. | |
| 2004/0006359 A1 | 1/2004 | Laguna | |
| 2004/0058603 A1 | 3/2004 | Hayes | |
| 2004/0082965 A1 | 4/2004 | Beckham | |
| 2004/0098120 A1 | 5/2004 | Williams et al. | |
| 2004/0109964 A1 | 6/2004 | Beckham | |
| 2006/0008606 A1 | 1/2006 | Horn et al. | |
| 2007/0106216 A1 | 5/2007 | Noddin | |
| 2009/0012610 A1 | 1/2009 | Olson et al. | |
| 2009/0099517 A1 | 4/2009 | Steadham | |
| 2010/0010438 A1 | 1/2010 | Simpson | |
| 2011/0046654 A1 | 2/2011 | Kuppurathanam | |
| 2012/0277783 A1 | 11/2012 | Cummins et al. | |
| 2012/0296363 A1 | 11/2012 | Davies, Jr. et al. | |
| 2013/0048200 A1 | 2/2013 | Pepper et al. | |
| 2013/0131709 A1 | 5/2013 | Davies, Jr. et al. | |
| 2013/0255866 A1 | 10/2013 | Beckham | |
| 2014/0166152 A1 | 6/2014 | Graves et al. | |
| 2014/0166193 A1 | 6/2014 | Pepper et al. | |
| 2014/0182738 A1 | 7/2014 | Simpson | |
| 2014/0243874 A1 | 8/2014 | Pepper et al. | |
| 2015/0081006 A1 | 3/2015 | Chuter et al. | |
| 2015/0374958 A1 | 12/2015 | Khieu et al. | |
| 2016/0136397 A1 | 5/2016 | Konstantino et al. | |
| 2016/0151611 A1 | 6/2016 | Pepper et al. | |
| 2017/0043119 A1 | 2/2017 | Kubo et al. | |
| 2017/0291014 A1 | 10/2017 | Royer et al. | |

FOREIGN PATENT DOCUMENTS

| | | |
|---|---|---|
| EP | 1388346 A1 | 2/2004 |
| EP | 1189553 B1 | 3/2004 |
| WO | 9803218 A1 | 1/1998 |
| WO | 2004028407 A1 | 4/2004 |
| WO | 2004050140 A2 | 6/2004 |
| WO | 2010051488 A1 | 5/2010 |

OTHER PUBLICATIONS

International Search Report and Written Opinion dated Sep. 4, 2017 for International Application No. PCT/US2017/037347.
International Search Report and Written Opinion for Application No. PCT/US2017/065853, 12 pages, dated Mar. 23, 2018.

MEDICAL BALLOON

CROSS REFERENCE TO RELATED APPLICATIONS

This application claims the benefit of U.S. Provisional Patent Application Ser. No. 62/433,730 filed on Dec. 13, 2016, the disclosure of which is incorporated herein by reference.

TECHNICAL FILED

The present disclosure pertains to medical devices and methods for manufacturing medical devices, for example, medical balloons.

BACKGROUND

Medical balloons can be used to administer a variety of treatments. For example, in an angioplasty procedure, a balloon can be used to widen a constricted bodily vessel, such as an artery, for example, a coronary artery. A balloon can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn.

BRIEF SUMMARY

This disclosure provides design, material, manufacturing method, and use alternatives for medical devices.

In one aspect, the present disclosure relates to a composite expandable medical balloon, the composite expandable medical balloon comprising a base balloon comprising at least one layer of an elastomeric polymer, the base balloon comprising a distal waist portion, a distal cone portion, a body portion, a proximal cone portion, and a proximal waist portion, a fiber braid disposed along the base balloon, the fiber braid comprising at least one polymeric fiber disposed over the base balloon, wherein the base balloon has a first length prior to heat sterilization of the composite expandable medical balloon, the first length being defined between a distal end of the distal waist portion and a proximal end of the proximal waist portion, wherein the base balloon is designed to have a second length after heat sterilization of the composite expandable medical balloon, the second length being defined between the distal end of the distal waist portion and the proximal end of the proximal waist portion, and wherein the second length is at least 95% of the first length.

Alternatively or additionally to any of the embodiments above, the second length is at least about 97% of the first length.

Alternatively or additionally to any of the embodiments above, the at least one layer of an elastomeric polymer comprises a polyether-block-amide block copolymer.

Alternatively or additionally to any of the embodiments above, the at least one polymeric fiber comprises an aromatic polyester liquid crystal polymer fiber.

Alternatively or additionally to any of the embodiments above, the at least one polymeric fiber comprises an aromatic polyamide copolymer fiber.

Alternatively or additionally to any of the embodiments above, the at least one polymeric fiber comprises an ultra high molecular weight polyethylene fiber.

Alternatively or additionally to any of the embodiments above, the composite expandable medical balloon further comprises at least one first layer comprising a thermoplastic polymer, the at least one first layer being disposed between the fiber braid and an outer surface of the base balloon.

Alternatively or additionally to any of the embodiments above, the at least one first layer comprises a thermoplastic polyurethane.

Alternatively or additionally to any of the embodiments above, the composite expandable medical balloon further comprises at least one second layer, the at least one second layer comprising a thermoplastic polymer, the at least one second layer being disposed along an outer surface of the fiber braid.

Alternatively or additionally to any of the embodiments above, the at least one second layer comprises a thermoplastic polyurethane.

Alternatively or additionally to any of the embodiments above, the base balloon has a first diameter prior to heat sterilization of the composite expandable medical balloon, wherein the base balloon has a second diameter after heat sterilization of the composite expandable medical balloon and wherein the second diameter is at least 95% of the first diameter.

In another aspect, the present disclosure relates to a composite expandable medical balloon, the composite expandable medical balloon comprising a heat set base balloon comprising at least one layer of an elastomeric polymer material, the heat set base balloon comprising a distal waist portion, a distal cone portion, a body portion, a proximal cone portion, and a proximal waist portion, wherein the heat set base balloon has a first length defined by a distal end of the distal waist portion and a proximal end of the proximal waist portion, a fiber braid comprising at least one polymeric fiber disposed over the heat set base balloon and wherein the heat set base balloon is designed to reduce or minimize delamination and tenting of the fiber braid from the base balloon during heat sterilization, after heat sterilization, or both.

Alternatively or additionally to any of the embodiments above, the composite expandable medical further comprises at least one first layer disposed between the heat set base balloon and the fiber braid, the at least one layer comprising a thermoplastic material and further comprising at least one second layer disposed on the fiber braid, the at least one second layer comprising a thermoplastic polymer material.

Alternatively or additionally to any of the embodiments above, the heat set base balloon comprises polyether-block-amide, the fiber braid comprises an aromatic liquid crystal polymer and the at least one first layer comprises a thermoplastic polyurethane.

In another aspect, the present disclosure relates to a method of forming a composite expandable medical balloon, the method comprising forming a base balloon comprising at least one layer of an elastomeric polymer, the base balloon comprising a distal waist portion, a distal cone portion, a body portion, a proximal cone portion and a proximal waist portion, heat setting the base balloon at a temperature of greater than about 110° C., disposing a fiber braid comprising at least one polymeric fiber along the base balloon to form the composite expandable medical balloon and sterilizing the composite expandable medical balloon at a temperature of at least about 40° C. or greater, wherein the base balloon has a first length prior to sterilizing the composite expandable medical balloon, the first length being defined between a distal end of the distal waist portion and a proximal end of the proximal waist portion, wherein the base balloon has a second length after sterilizing the composite expandable medical balloon, the second length being defined between the distal end of the distal waist portion and the proximal end of the proximal waist portion, and wherein the second length is at least about 95% of the first length.

Alternatively or additionally to any of the embodiments above, the second length is at least about 97% of the first length of the base balloon.

Alternatively or additionally to any of the embodiments above, heat setting the base balloon at a temperature of greater than about 110° C. comprises heat setting the base balloon at a temperature of greater than about 115° C.

Alternatively or additionally to any of the embodiments above, sterilizing the composite expandable medical balloon at a temperature of at least about 40° C. or greater comprises sterilizing the composite expandable medical balloon with ethylene oxide.

Alternatively or additionally to any of the embodiments above, the elastomeric polymer is a polyether-block-amide.

Alternatively or additionally to any of the embodiments above, the at least one polymeric fiber is an aromatic polyester liquid crystal polymer fiber.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

The materials that can be used for the various components of the medical devices disclosed herein and the components thereof may include those commonly associated with medical devices, some of which are listed below.

A number of medical balloons may include a balloon or "base balloon" with a reinforcement such as a fiber braid disposed thereon. It may be desirable for the fiber braid to be secured to the base balloon in a manner such that the bond between the fiber braid and the base balloon is maintained, for example after heat sterilization of the braided balloon. For example, braided balloon designs may exhibit delamination of the fiber braid from the base balloon as well as to delamination from the base balloon of any subsequent layers, for example, other polymer layers disposed between the fiber braid, the base balloon, or disposed over the fiber braid. Base balloons, for example, elastomeric base balloons may exhibit recoil or shrinkage during the plasma treatment, oven annealing, and/or heat sterilization processes which can result in a shorter length and/or smaller diameter. This can lead to delamination of the fiber braid from the base balloon as well as delamination of any subsequent layers between the base balloon and fiber braid or disposed over the fiber braid, from the base balloon, and which may further result fiber movement and bulging at the cones. Delamination of the layers, particularly when other polymer layers are present can result in pockets forming between the base balloon and the fiber braid. These pockets can fill with fluid when the braided balloon is deflated, and even when the balloon is fully deflated. When a braided balloon with delamination pockets is inflated, liquid that is trapped in the pockets may be compressed resulting in even larger pockets, and consequently, leaking or escaping of fluid from the spaces or windows that exist between the fibers that form the fiber braid. Trapped liquid between the base balloon and the fiber braid and/or subsequent layers may cause higher withdrawal forces from a sheath and may also result in reduced performance, such as lower burst pressure.

The present disclosure relates to a composite expandable medical balloon having a base balloon having at least one elastomeric layer and a fiber braid disposed thereon that exhibit rated burst strengths of 30 atmospheres or higher, for example 35-70 atmospheres.

Figure 1:
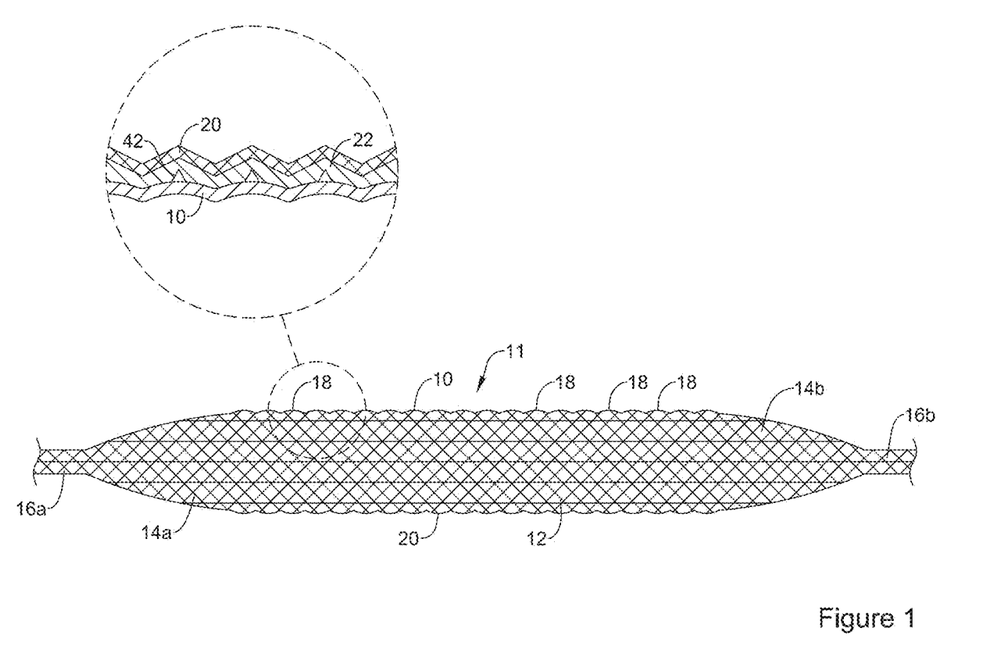
FIG. 1 is a side view of a comparative example medical device.

FIG. 1 is a side view of a comparative example medical device. The medical device is, for example, a hybrid or composite balloon 11 including a base balloon 10 shown having a body portion 12, a proximal cone portion 14a, a distal cone portion 14b, a proximal waist portion 16a, and a distal waist portion 16b. A fiber braid 20 may be disposed along the outer surface of the base balloon 10. The fiber braid 20 includes windows 18 defined between the fibers of the fiber braid 20.

The composite balloon 11 may be secured to a tubular member, for example, a catheter shaft (not shown) at the proximal waist portion 16a and the distal waist portions 16b, respectively as discussed in more detail below.

During manufacturing of the base balloon 10, the fiber braid 20 may delaminate from the base balloon 10 resulting in tenting or pillowing of the fiber braid 20 that may lead to gaps or pockets 42 that form between the base balloon 10 and the fiber braid 20 where the fiber braid 20 has delaminated from the base balloon 10. Cone bulging (not shown) may also occur. While the pillowing of the fiber braid 20 from the base balloon 10 is shown in the body portion 12 of the base balloon 10, this is just an example and may occur at any location on the balloon, for example, the pillowing may also extend into the proximal cone portion 14a and the distal cone portion 14b. This may occur for example, during the manufacturing/processing steps at elevated temperatures, for example, during plasma treatment or heat sterilization involving the composite balloon 11 wherein the fiber braid 20 is disposed over the base balloon 10. When the composite balloon 11 is deflated subsequent to manufacturing, the pockets 42, may fill with fluid, and when the composite balloon 11 is subsequently inflated, the liquid present, for example, that is trapped in the pockets 42 may be compressed or squeezed resulting in an increase in size of the pockets 42 that may further result in leaking or weeping of the fluid from the pockets 42 and into the windows 18 defined between the fibers of the fiber braid 20.

Figure 2:
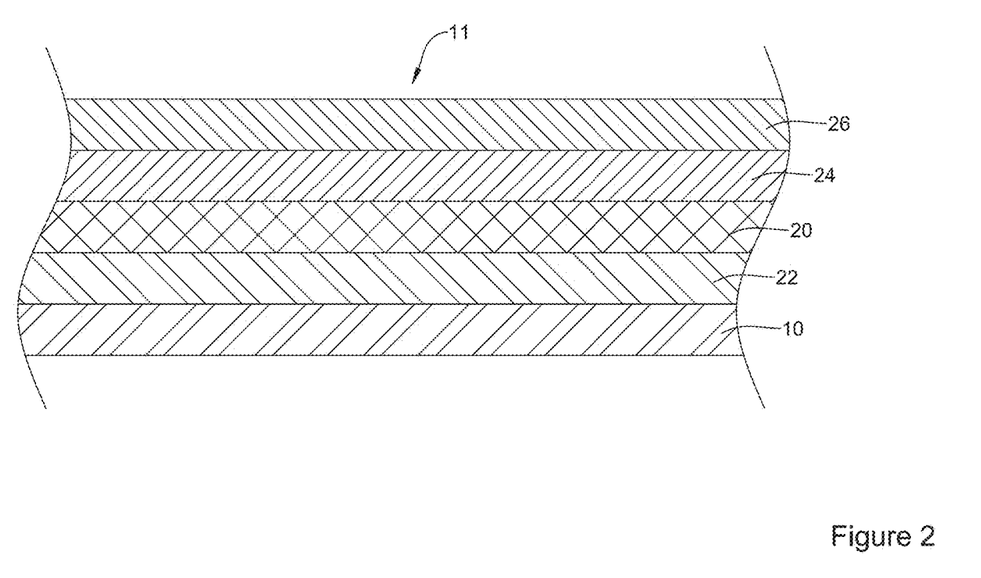
FIG. 2 is a cross-section of a portion of an example medical device.

In some embodiments, a layer 22 may be disposed between the base balloon 10 and the fiber braid 20, as shown in the enlarged portion of FIG. 1, for example, to improve adhesion of the fiber braid 20 to the base balloon 10. The fiber braid 20, which is disposed on and in contact with the layer 22 during delamination, may pull the layer 22 away from the base balloon leaving pockets 42 between the base balloon 10 and the layer 22. Additional layers may be included, which would subsequently be affected by the fiber braid 20 delaminating from the base balloon 10 as well. For example, FIG. 2 schematically depicts some of the layers contemplated. For example, the example composite balloon 11 may include the base balloon 10, the layer 22 disposed between the base balloon 10 and the fiber braid 20, the fiber braid 20, a layer 24 which may be formed from the same or from a different polymer material than that of the layer 22, and an outer layer 26, for example, a lubricious coating layer. In some embodiments, the layer 22 and the layer 24 are formed of the same material and form, for example, a matrix around the fiber braid 20. These are just examples. Other composite balloons are contemplated that include more or few layers, layers arranged differently than what is shown in FIG. 2.

As indicated above, delamination of the fiber braid 20 from the base balloon 10 may occur during heat processing steps. In some instances, pockets 42 may form between the layer 22 and the base balloon. When more low viscosity materials, for example solvents or a lubricious liquid material, are employed, for example as the outer layer 26, the lubricious liquid material may migrate or ingress into the pockets 42 formed between the layer 22 and the base balloon 10 (e.g., during a heat sterilization process). The material trapped in the pockets 42 can cause higher withdrawal forces from a catheter or sheath after use and may result in reduced performance, for example, lower burst pressure due to the poor fiber braid 20 and the matrix (layers 22, 24) integrity.

Figure 3:
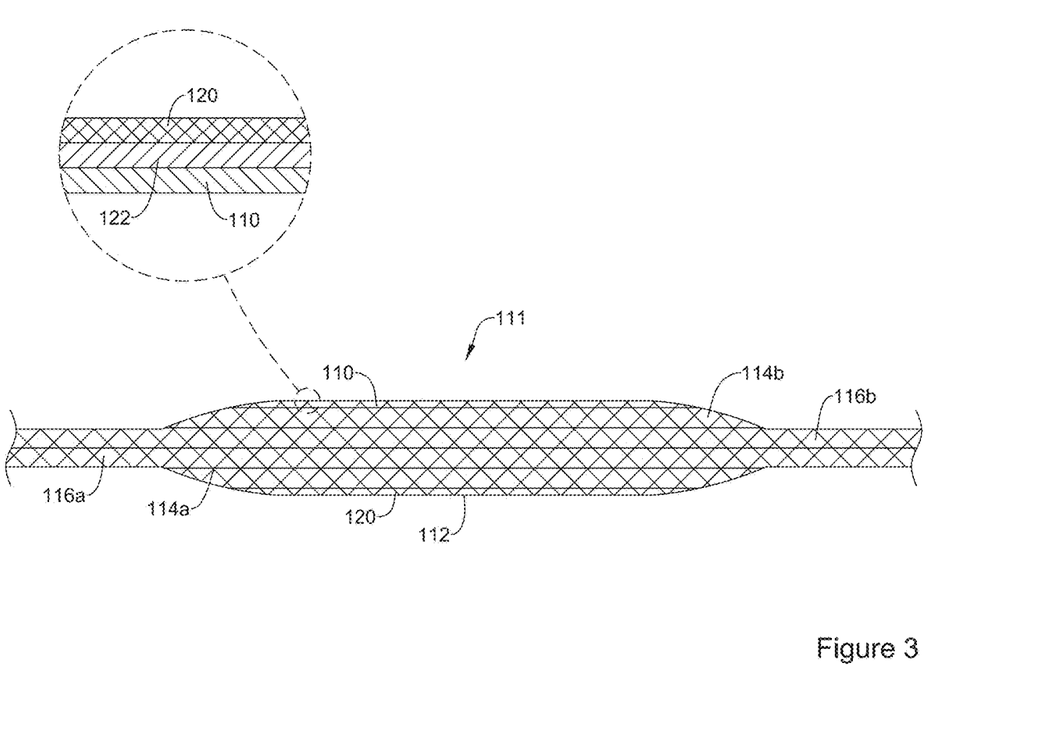
FIG. 3 is a side view of an example medical device.

The present disclosure is directed to composite balloons, for example, composite balloons 111, wherein the base balloon 110 may include an elastomeric polymer layer as shown in FIG. 3. The base balloon includes a proximal waist portion 116a, a proximal cone portion 114a, a body portion 112, a distal cone portion 114b and a distal waist portion 116b. The example composite balloons 111 may exhibit reduced delamination of the fiber braid 120 from the base balloon 110 (e.g., as represented in FIG. 3). In some of these and in other instances, the composite balloon 111 may exhibit reduced delamination of any additional layers that might be disposed between the base balloon 110 and the fiber braid 120. For example, the composite balloon 111 may include one or more additional layers such as a layer 122 disposed between the base balloon 110 and the fiber braid 120. The composite balloon 111 may exhibit reduced delamination between the layer 122 and the base balloon 110.

Figure 4:
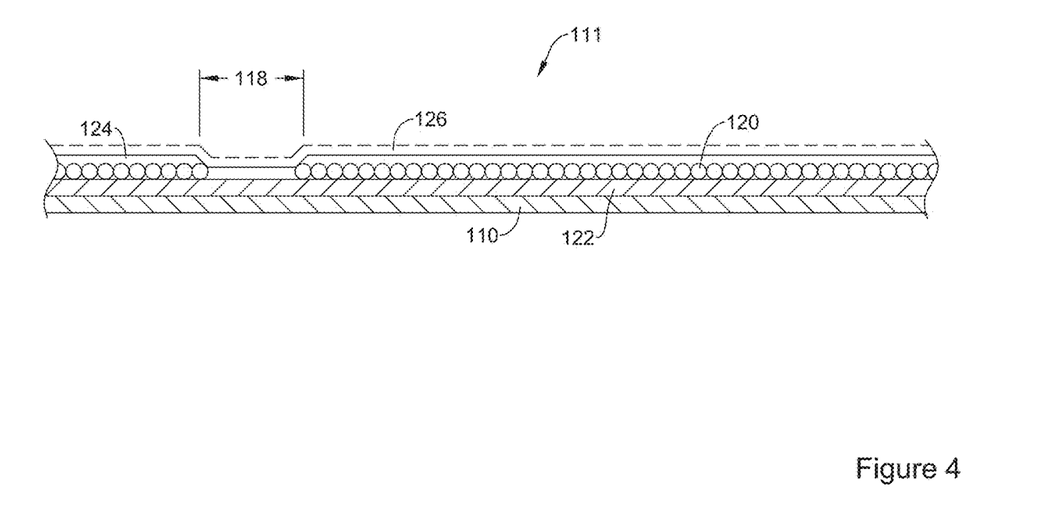
FIG. 4 is a partial cross-sectional side view of an example medical device.

FIG. 4 is a partial cross-sectional view of the composite balloon 111. Some of the layers contemplated for the composite balloon 111 can be seen such as, for example, the base balloon 110, the layer 122, the fiber braid 120, a layer 124, and optionally an outer layer 126. As discussed above, the composite balloon 111 may incorporate fewer layers or even more layers if desired. Any combination of layers is contemplated herein. For example, the base balloon 110 and the fiber braid 120; or the base balloon 110, the layer 122 and the fiber braid 120; or the base balloon 110, the layer 122, the fiber braid 120 and the layer 124; or the base balloon 110, the layer 122, the fiber braid 120, the layer 124 and the layer 126 or any other combination thereof. The fiber braid 120 includes windows 118 between the fiber braid 120 wherein the base balloon 110 and, optionally, the layer 122 are exposed. When the base balloon 110 includes the layer 124 and/or the layer 126, the thickness of the composite balloon 111 may have a lesser wall thickness than the portions of the composite balloon 111 where the fiber braid 120 is present as shown in the FIG. 4.

The base balloon 110 may be formed from a polymer material, for example at least one layer including an elastomeric polymer material. As used herein, an elastomeric polymer material may be understood to refer to polymers that are suitable for use in making expandable medical balloons, for example, elastomeric block copolymers having at least one soft block and at least one hard block, for example, block copolymers comprising at least one polyester, polyether, polyamide or polyurethane block. Suitable elastomeric polymers are discussed in more detail below. In some embodiments, the base balloon 110 is formed from at least one layer of a polyether-block-amide block copolymer. In some embodiments, the base balloon 110 is formed from a polyether-block-amide copolymer and the fiber braid 120 is formed from a Vectran® liquid crystal polymer (LCP) fiber, for example, an aromatic polyester LCP fiber, an ultra high molecular weight polyethylene fiber, an Aramid fiber, or combinations thereof. Materials employed to form the base balloon 110, the fiber braid 120, and any additional layers, are discussed in more detail below. It is also contemplated that other layers may be employed in forming the base balloon, for example, a polyamide layer may be included. The fiber braid 120 may be formed from a polymer material, for example, a polymer material that provides high strength and high modulus. In at least some instances, the base balloon 110 may be formed from an elastomer, for example, a polyether-block-amide. The layer 122 may be formed from a low durometer, friction-enhancing thermoplastic polymer, for example, a thermoplastic polyurethane, the fiber braid 120 may be formed from an aromatic polyester LCP fiber, the layer 124 may be formed from a thermoplastic polymer, for example, a thermoplastic polyurethane, and the outer layer 126 may be a lubricious coating layer.

Figure 5:
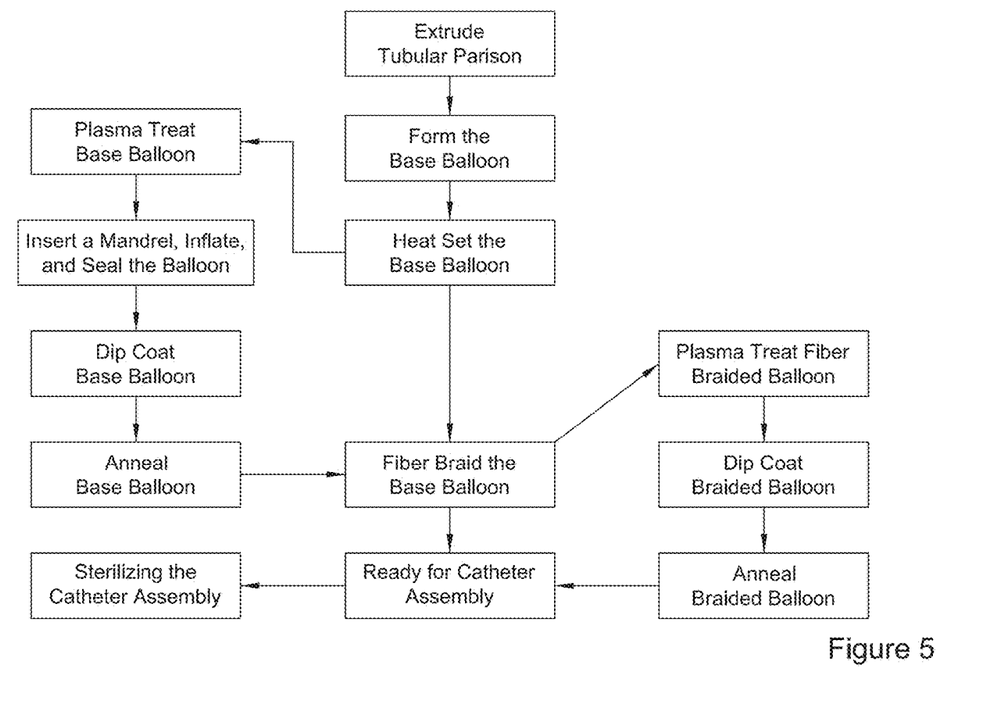
FIG. 5 is a process flow diagram illustrating an example method of forming an example medical device.

FIG. 5 is a block flow diagram illustrating an example method of making the example composite balloon 111. Generally, as illustrated at block number 1, a tubular parison of a suitable polymer material (e.g., elastomeric polymer material) is extruded, and the base balloon 110 may be formed using conventional methods such as, for example, radial expansion of a tubular parison in a balloon mold as shown at block number 2. The base balloon 110 may be preformed, for instance, by radial expansion of a tubular parison, which is optionally also longitudinally stretched. The extruded parison may be radially expanded as is into a mold or by free-blowing. Alternatively, the parison may be pre-stretched longitudinally before expansion or reformed in various methods to reduce the thickness of the balloon cone and waist regions prior to radial expansion. The blowing process may utilize pressurization under tension, followed by rapid dipping into a heated fluid; a sequential dipping with differing pressurization; and a pulsed pressurization with compressible or incompressible fluid, after the material has been heated. Heating may also be accomplished by heating the pressurization fluid injected into the parison. Balloon diameters may range from 4 mm to 26 mm depending on the application, or about 4 mm to about 12 mm for some applications. In some embodiments, the tubular parison is radially expanded in a balloon mold subjected to a water bath at a temperature of less than about 100° C., for example, about 95° C. to form the base balloon 110.

The base balloon 110 may then be heat set by subjecting the base balloon 110 to an elevated temperature as shown at block number 3. The elevated temperature may be greater than 100° C., or about 110° C. to about 160° C., or in the range of about 115° C. to about 150° C., or in the range of about 115° C. to 145° C. to heat set the base balloon 110. In some instances, the base balloon 110 is heat set at 115° C., or 130° C., and in some embodiments the base balloon 110 is heat set at 145° C. For example, the mold may be removed from the water bath, placed in a heating device that uses an external heat source (e.g., electric heat) to heat the balloon mold, and the base balloon 110 is heat set at a temperature, for example, in the range of about 115° C. to about 145° C., or in the range of about 130° C. and in some embodiments, a temperature of about 145° C. is employed. The base balloons 10, for example, the base balloons 10 discussed with respect to FIG. 1, wherein the base balloon 10 has been molded in a water bath without an additional heat set step, may exhibit more delamination and tenting of the fiber braid 20 from the base balloon than those base balloons 110 that have been heat set as discussed herein.

Further, the fiber braid 120 is disposed on the base balloon 110 as shown at block number 4. Again, the layer 122, may be disposed on the base balloon 110 prior to the fiber braid 120, or any or all of layers 122, 124, 126, or any additional layers between the base balloon 110 and the fiber braid 120, or subsequent layers over the fiber braid 120 as well.

In some embodiments, an inflated and sealed base balloon 110 may be braided with Vectran® LCP fibers, commercially available from Kuraray, using a 32 carrier Steeger braider. An 8×100 mm base balloon 110 may for example, be braided using 32 carriers, each with 10 individual filaments, each filament being 25 µm in diameter, and 16 longitudinal carriers composed of 15 individual filaments, each filament being 25 µm in diameter.

In some embodiments, the base balloon 110, prior to application of the fiber braid 120, is subjected to a plasma treatment illustrated at block number 5. In some embodiments, after plasma treatment, a mandrel is inserted into the base balloon 110 shown at block number 6, the balloon is inflated, for example at a pressure of about 15 psi, and the proximal end of the proximal waist portion 116a and the distal end of the distal waist portion 116b are sealed. In some embodiments, the base balloon is further dip coated with a solution of a thermoplastic polymer material shown at block number 7, a thermoplastic polyurethane as further shown in FIG. 5.

At this point, as illustrated at block number 8, the base balloon may be subjected to an annealing process at an elevated temperature, for example, at a temperature in the range of about 60° C. to about 80° C. In some embodiments, wherein a polyurethane layer 122 or a polyurethane layer 124 are employed, the annealing is conducted at a temperature of about 70° C. The temperature of annealing is determined by the glass transition temperature ($T_g$) of the polymer layer 122 and/or 124 that is employed. The annealing temperature is not limited to the ranges disclosed herein and is determined by and set above the $T_g$ of the polymer layer employed.

After disposing the fiber braid 120 on the base balloon 110, the now fiber-braided composite balloon 111 may also be subjected to a plasma treatment shown at block number 9, and then once again dip coated with a solution of a thermoplastic polymer material, for example, a thermoplastic polyurethane as shown at block number 10. At this point, the composite balloon 111 may be subjected to an annealing process at an elevated temperature as shown at block number 11, for example, in the ranges provided above. The composite balloon 111 is now ready for catheter assembly illustrated at block number 12, and the entire assembly can be sterilized as illustrated at block number 13, for example, using ethylene oxide, at an elevated temperature(s). This may involve a heat sterilization cycle, for example, wherein the catheter assembly, for example, the catheter assembly 213 shown in FIG. 6 and discussed below, is sterilized using a suitable material, for example, ethylene oxide, at temperatures in the range of about 40° C. to about 100° C., or about 40° C. to about 80° C. or about 40° C. to about 60° C. In some embodiments, heat sterilization is conducted at temperatures of about 109° C. to about 135° C. using ethylene oxide. The total duration of heat sterilization may range from about 5 hours to about 35 hours, or from about 10 hours to about 30 hours or from about 15 hours to about 30 hours. In some embodiments, heat sterilization is conducted from about 16 to about 27 hours.

The present disclosure is directed to a balloon design that reduces the amount of shrinking or recoil of the base balloon 110 during heat sterilization which also reduces or minimizes delamination of the fiber braid 120 from the base balloon 110 and any subsequent layers, for example the layer 122, the layer 124, the layer 126, or combinations thereof, and any additional layers that may be present. It has been found that the additional step of heat setting the base balloon 110 at an elevated temperature reduces the amount of both the longitudinal and radial shrinkage of the base balloon 110 after heat sterilization which reduces or minimizes delamination of the fiber braid 120, tenting of the fiber braid 120 and pocket formation that may occur between the base balloon 110 and subsequent layers, for example the layer 122 and/or the layer 124.

Shrinkage of the base balloon 110 may be determined using the nominal or original length ($L_1$) of the base balloon 110 as defined to be between the proximal end of the proximal waist portion 116a and the distal end of the distal waist portion 116b and the nominal or original diameter ($D_1$) of the body portion 112 of the base balloon 110 as it is removed from the balloon mold, and the length ($L_2$) as defined to be between the proximal end of the proximal waist portion 116a and the distal end of the distal waist portion 116b and diameter ($D_2$) of the body portion 112 of the composite balloon 111 after heat sterilization. The percent shrinkage may be determined using the following formulas:

Percent Length Shrinkage=$[(L_1-L_2)/L_1] \times 100$ and
Percent Diameter Shrinkage=$[(D_1-D_2)/D_1] \times 100$ The effect of the heat set on the composite balloon 111 may be compared to composite balloons 11, such as those described with respect to FIG. 1 above, that were not subjected to a heat set, but were simply molded in a water bath at temperatures of less than 100° C., for example, 95° C. with no additional heat set step. The composite balloons 111 where the base balloon 110 was subjected to a heat set exhibit in the range of about 1% to about 10% less shrinkage in length (as defined between the proximal end of the proximal waist portion 116a and the distal end of the distal waist portion 116b) and/or diameter (e.g., the diameter at the body portion 112 of the base balloon 110) after heat sterilization than composite balloons (e.g., the composite balloons 11) wherein the base balloon (e.g., the base balloon 10) was not subjected to a heat set. In other words, the composite balloons 111 subjected to a heat set as disclosed herein, exhibit about 1-10% less axial and/or radial shrinkage, or about 1-8% less axial and/or radial shrinkage, or about 3-6% less axial and/or radial shrinkage, or about 6% less axial and/or radial shrinkage, or about 3% less axial and/or radial shrinkage than composite balloons not heat set in the manner disclosed herein.

In addition and/or stated another way, the base balloon 110 (e.g., that is heat set in the manner disclosed herein) may have a first length (e.g., defined between a proximal end of the proximal waist portion 116a and a distal end of the distal waist portion 116b) prior to heat sterilization and the base balloon 110 may have a second length (e.g., also defined between a proximal end of the proximal waist portion 116a and a distal end of the distal waist portion 116b) after heat sterilization. The second length may be about 90% or more of the first length, or about 95% or more of the first length, or about 97% or more of the first length.

The composite balloon 111 may be capable of being inflated to relative high pressures. For example, the composite balloon 11 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. Furthermore, the bond between the fiber braid 120 and the base balloon 110 is also maintained at these elevated pressures reducing or minimizing delamination between the fiber braid 120 and the base balloon 110.

In some embodiments, the base balloon 110 may be formed from poly(ether-block-amide) copolymers. The polyamide/polyether block copolymers are commonly identified by the acronym PEBA (polyether block amide). The polyamide and polyether segments of these block copolymers may be linked through amide linkages, for example, some are ester linked segmented polymers, e.g., polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. Polymers of this type are commercially available under the tradename of Pebax® from Arkema. Specific examples are the "33" series polymers with hardness 60 and above, Shore D scale, for example, Pebax® 6333, 7033 and 7233. These polymers are made up of nylon 12 segments and poly(tetramethylene ether) segments linked by ester groups.

Polyester/polyether segmented block copolymers may also be employed herein. Such polymers are made up of at least two polyester and at least two polyether segments. The polyether segments are the same as previously described for the polyamide/polyether block copolymers useful in the disclosure. The polyester segments are polyesters of an aromatic dicarboxylic acid and a two to four carbon diol.

In some embodiments, the polyether segments of the polyester/polyether segmented block copolymers are aliphatic polyethers having at least 2 and no more than 10 linear saturated aliphatic carbon atoms between ether linkages. The ether segments may have 4-6 carbons between ether linkages, and they may include poly(tetramethylene ether) segments. Examples of other polyethers which may be employed in place of the tetramethylene ether segments include polyethylene glycol, polypropylene glycol, poly (pentamethylene ether) and poly(hexamethylene ether). The hydrocarbon portions of the polyether may be optionally branched. An example is the polyether of 2-ethylhexane diol. Generally, such branches will contain no more than two carbon atoms. The molecular weight of the polyether segments is suitably between about 400 and 2,500, and more suitably between 650 and 1000.

In some embodiments, the polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Specific examples of polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

The fiber braid 120 may be formed from a variety of suitable materials. Some specific examples include, but are not limited to, polyesters such as polyethylene terephthalate (PET), polybutylene terephthalate (PBT), and polytrimethylene terephthalate (PTT). Polyamides include nylons and aramids such as Kevlar®. Polyolefins include ultra high molecular weight polyethylene, and very high density polyethylene, and polypropylene fibers. Combinations of fibers are also contemplated. In some specific embodiments of the disclosure, fibers that are high strength materials may also be suitable in some applications.

In some embodiments, the fiber braid 120 is formed using a high melting temperature fiber, for example, a liquid crystal polymer, for example, Vectran®, an aromatic polyester available from Kuraray Ltd., USA, and having their headquarters located in Tokyo, Japan. In some embodiments, the liquid crystal polymer is formed by the polycondensation of 4-hydroxybenzoic acid and 6-hydroxynaphthalene-2-carboxylic acid.

The fiber braid 120 may also be formed from an ultra high molecular weight polyethylene (UHMPE). Commercially available UHMPEs include, but are not limited to, Dyneema® fiber available from DSM Dyneema BVm Heerlen, Netherlands, Spectra® fiber available from Honeywell in Morristown and Pegasus UHMWPE fiber available from Pegasus Materials in Shanghai, China.

The fiber braid 120 may also be formed from a copolyamide, for example, Aramid fiber. Aramid fiber are aromatic polyamides and can be classified as heat-resistant, non-melting fibers wherein degradation starts from 500° C. Typically, aramids are long-chain polyamides wherein at least 85% of the amide linkages are attached to two aromatic rings. Many of these materials are classified as having no melting point. One commercially available aramid fiber is Technora®, para-aramid which is a polyamide copolymer. Technora® fiber is available from Teijin Aramid, a subsidiary of the Teijin Group in the United Kingdom. Other examples of suitable aramid fibers include, but are not limited to, Kevlar® fiber available from DuPont in Wilmington, Del., Nomex® meta-aramid fiber also available from DuPont, and Twaron fiber which is also available from Teijin Aramid.

Figure 6:
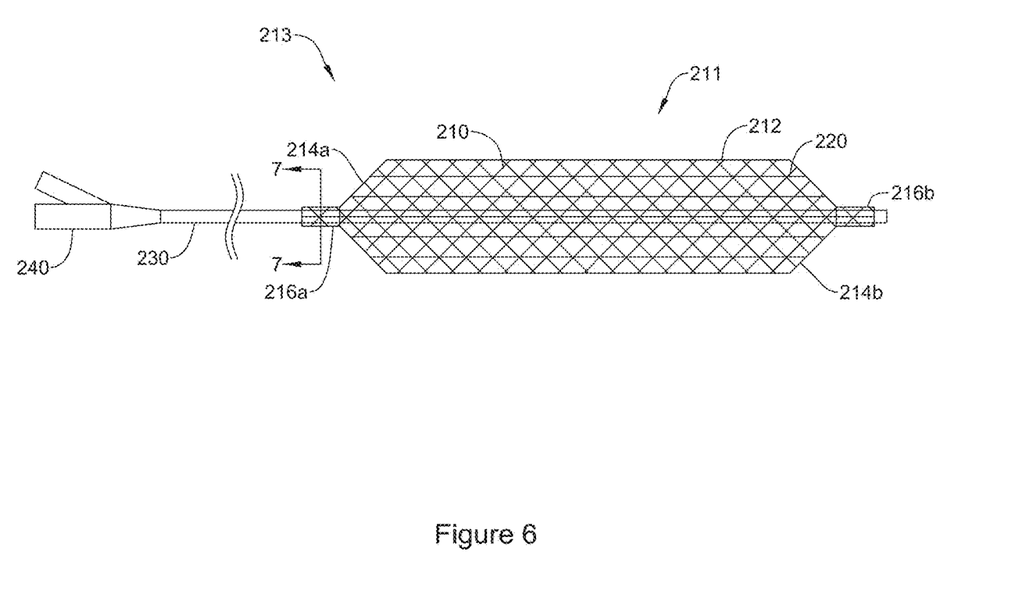
FIG. 6 is a side view of an example medical device.

A side view of an exemplary balloon catheter 213 is illustrated in FIG. 6 with a composite balloon 211 assembled on the balloon catheter 213. The composite balloon 211 may be mounted on the distal end of a catheter shaft 230. The composite balloon 211 may be the same as or similar to the composite balloon 111, as shown and described with reference to FIGS. 3-5. A fiber braid 220 may be disposed along the outer surface of the base balloon 210. Catheter shaft 230 extends from a manifold assembly 240 at a proximal end of the catheter shaft 230. The balloon 211 is shown having a body portion 212, a proximal cone portion 214a, a distal cone portion 214b, a proximal waist portion 216a, and a distal waist portion 216b. The balloon 211 may be secured to the catheter shaft 230 at the proximal waist portion 216a and the distal waist portions 216b, respectively.

Figure 7:
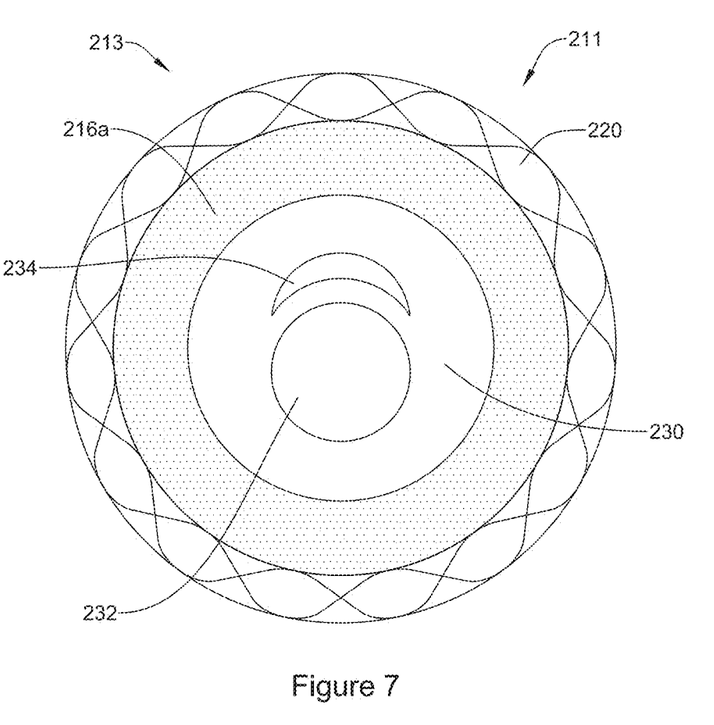
FIG. 7 is a cross-section of an example medical device taken at section 7-7 in FIG. 6.

FIG. 7 is a cross-sectional view of the balloon catheter 213 taken at section 7-7 of FIG. 6. The catheter shaft 230 is depicted as a dual-lumen catheter shaft 230 that includes a guidewire lumen 232 for a guidewire and an inflation lumen 234 for inflation of the composite balloon 211. Alternatively, the catheter shaft 230 may include an inner tubular member defining the guidewire lumen 232 and an outer tubular member extending around the inner tubular member. In these instances, the inflation lumen 234 may be defined between the inner tubular member and the outer tubular member. In such cases, the proximal waist portion 216a may be secured to a distal end region of the outer tubular member and the distal waist portion 216b may be secured to a distal end region of the inner tubular member. Other catheter shafts are contemplated.

The composite balloon 211 may be capable of being inflated to relatively high pressures. For example, the composite balloon 211 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. At such elevated pressures, the bond between the proximal waist portion 216a and the catheter shaft 230, as well as the bond between the distal waist portion 216b and the catheter shaft 230 is maintained. Furthermore, the bond between the fiber braid 220 and the base balloon 210 is also maintained at these elevated pressures reducing or minimizing delamination between the fiber braid 220 and the base balloon 210.

The catheter shaft 230 may be formed from any suitable shaft material. Examples include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the catheter shaft 230 can be formed by also blending a polymer material a liquid crystal polymer (LCP). For example, the shaft material mixture can contain up to about 6 percent LCP. In some embodiments, the catheter shaft 230 is formed from a polyamide, for example Grilamid® which is commercially available from EMS-Grivory.

The above lists are intended for illustrative purposes only, and not as a limitation on the present disclosure. It is within purview of those of ordinary skill in the art to select other polymers without departing from the scope of this disclosure.

EXAMPLES

Example 1

A tubular parison was extruded with a monolayer of Pebax 7033. The Pebax 7033 tubular parison having a 8×100 mm diameter and length was stretched, placed in a balloon mold, and radially expanded while the balloon mold was in a water bath at 95° C. to form a base balloon.

The balloon mold with the base balloon still disposed therein, was then removed from the water bath, placed in a heating device having an electric heat source, and heated at an elevated temperature. Some base balloons were heat set at a temperature of about 115° C. and some of the base balloons tested were heat set at a temperature of about 145° C. A stainless steel mandrel was inserted in the base balloon. The balloon was inflated to 15 psi and the proximal end and the distal end of the balloon were sealed.

The balloon was plasma treated with $ArO_2$ gas, and dip coated with 2.5% solids Lubrizol SG 60D thermoplastic polyurethane in a cosolvent blend of 50% toluene/50% tetrahydrofuran. The plasma treatment was conducted in a Nordson-March RF Plasma Chamber at a 100 sccm $ArO_2$ flow rate, base pressure 100 mtorr, 250 watts, 90 seconds times three cycles. The coating thickness was approximately 6 µm. The dipping process may take up to three repeat cycles to achieve the desired thickness with 10 minutes in between each cycle, at a dip down and up speed of 50 inches/minute, and with a hold time of 2 seconds in a 100 ml graduated cylinder.

The base balloon was then annealed at 70° C. for 10 minutes.

The balloon was again plasma treated with $ArO_2$ gas, and dip coated with 2.5% solids Lubrizol SG 60D thermoplastic polyurethane in a cosolvent blend of 50% toluene/50% tetrahydrofuran. The plasma treatment was conducted in a Nordson-March RF Plasma Chamber at a 100 sccm $ArO_2$ flow rate, base pressure 100 mtorr, 250 watts, 90 seconds times four cycles. The thickness of the top polyurethane layer was approximately 6 µm. The dipping process may take up to eight repeat cycles to achieve the desired thickness with 10 minutes in between each cycle, at a dip down and up speed of 50 inches/minute, with a hold time of 2 seconds.

The composite balloon was again annealed at 70° C. for 10 minutes.

The balloon waists were trimmed, the mandrel removed and the composite balloon would be ready for catheter assembly and sterilization.

The composite balloons were sterilized in a temperature range of about 40° C. to about 60° C. for about 16 to about 27 hours using ethylene oxide.

The composite balloon was tested for the impact of heat set on the balloon length and on the balloon diameter and compared to balloons that were formed as described above, without the additional heat set step or wherein the balloon has been molded only in the 95° C. water bath.

As discussed above, shrinkage of the base balloon may be determined using the nominal or original length ($L_1$) and the nominal or original diameter ($D_1$) of the balloon as it is removed from the balloon mold, and the length ($L_2$) and diameter ($D_2$) of the composite balloon 111 after heat sterilization. The percent shrinkage may be determined using the following formulas:

$$\text{Percent Length Shrinkage}=[(L_1-L_2)/L_1]\times 100 \text{ and Percent Diameter Shrinkage}=[(D_1-D_2)/D_1]\times 100$$

Figure 8:
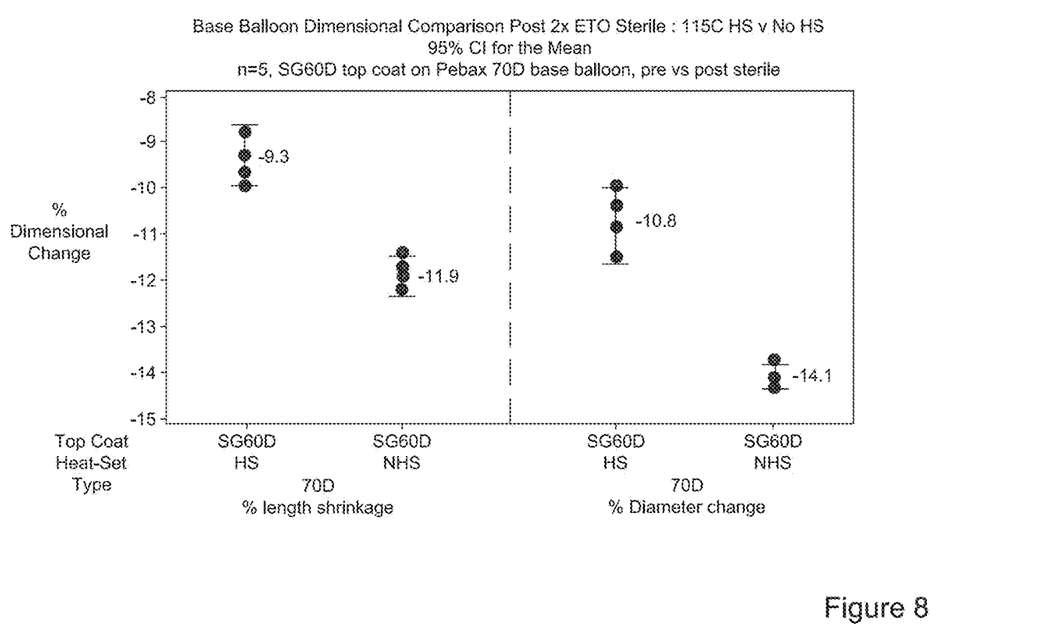
FIG. 8 is a graph illustrating the impact of a heat-set on the length of an example medical balloon.

FIG. 8 is a graph illustrating the effect on the amount of shrinkage in the length of the base balloon wherein the base balloon has been heat set (HS) at a temperature of about 115° C. as compared to a base balloon that has been molded in a 95° C. water bath with no additional heat set step (NHS). As can be seen by the graph, the sterilized composite balloons wherein the base balloon was heat set (HS), exhibited 3% less shrinkage in length than sterilized composite balloons with no heat set (NHS) base balloon.

It was further found that heat setting a base balloon at a temperature of about 145° C. compared to a base balloon that has been molded in a 95° C. water bath with no additional heat set step, reduced the amount of shrinkage in the length to a greater extent. Sterilized composite balloons wherein the base balloon was heat set at 145° C., exhibited about 6% less shrinkage than base balloons that were heat set at 115° C.

Figure 9:
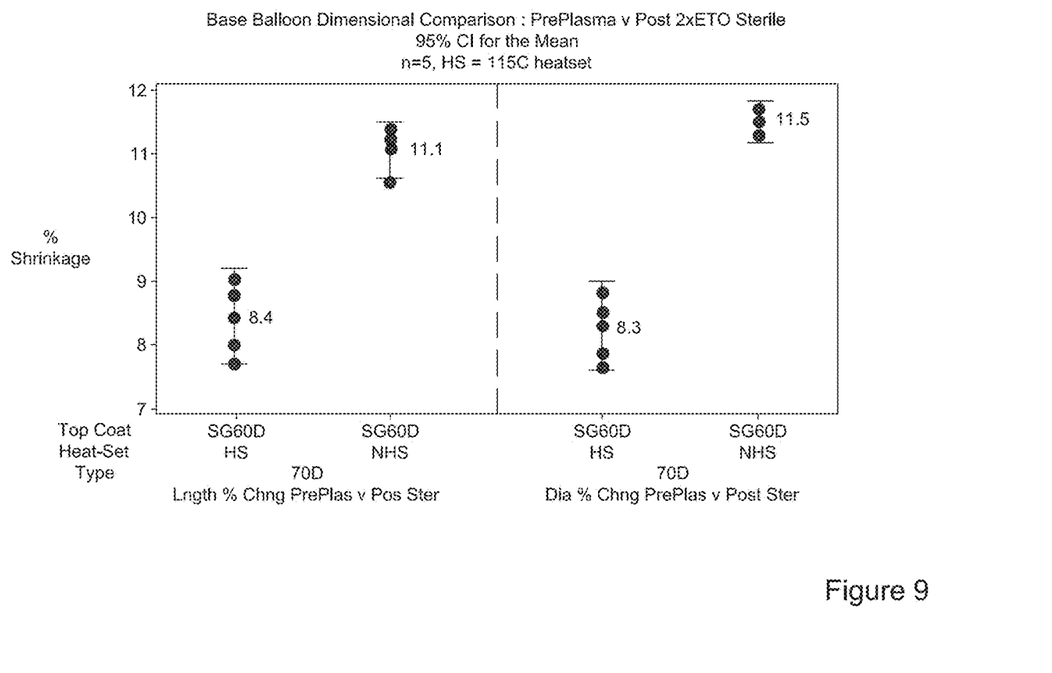
FIG. 9 is a graph illustrating the impact of a heat-set on the diameter of an example medical balloon.

FIG. 9 is a graph illustrating the effect on the amount of shrinkage in the diameter of the base balloon wherein the base balloon with the polyurethane layers has been heat set (HS) at a temperature of about 115° C. as compared to a base balloon that has been molded in a 95° C. water bath with no additional heat set (NHS) step. As can be seen by the graph, the sterilized composite balloons wherein the base balloon was heat set (HS), exhibited 3% less shrinkage in diameter than sterilized composite balloons with no heat set (NHS) base balloon.

It was further found that heat setting a base balloon at a temperature of about 145° C. compared to a base balloon that has been molded in a 95° C. water bath with no additional heat set step reduced the amount of shrinkage in the diameter to a greater extent. Sterilized composite balloons wherein the base balloon was heat set at 145° C. exhibited about 6% less shrinkage in diameter than base balloons that were heat set at 115° C.

Figure 10:
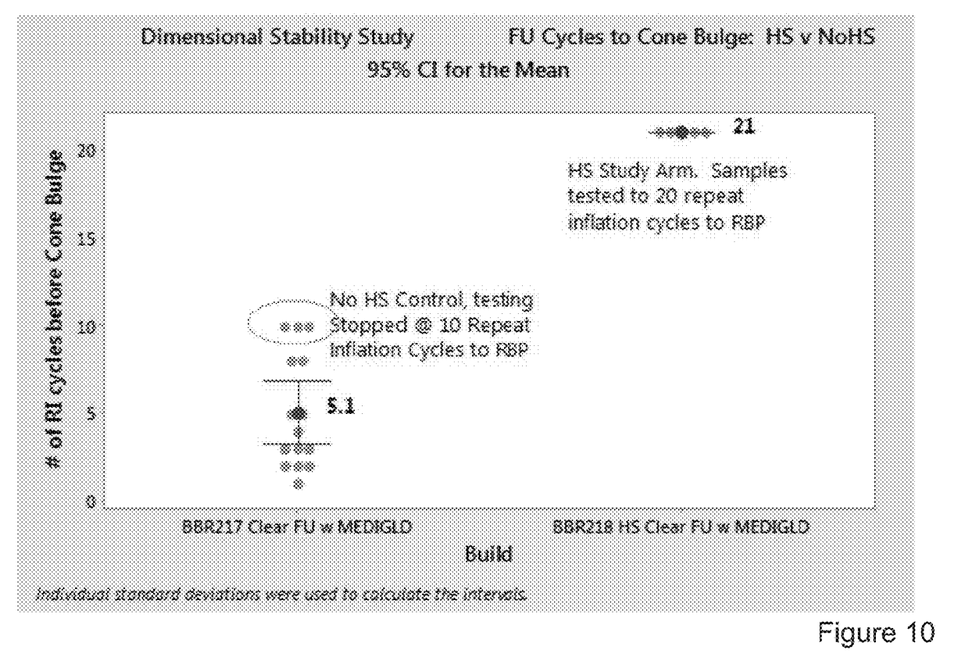
FIG. 10 is a graph illustrating the impact of a heat-set on the dimensional stability of an example medical balloon.

FIG. 10 is a graph illustrating the effect on the occurrence of cone bulging upon repeat inflation bench testing to the catheters rated burst pressure of the base balloon wherein the base balloon has been heat set (HS) at a temperature of about 115° C., as compared to a base balloon that has been molded in a 95° C. water bath with no additional heat set (NHS) step. The balloon was inflated to the rated burst pressure from one to twenty cycles. Cone bulging occurred between the first inflating cycle and up to the tenth repeat inflation cycle in the base balloons molded at 95° C. with no additional heat set step (NHS). The base balloons that were heat set (HS) at 115° C. exhibited no cone bulging even at the twentieth repeat inflation cycle.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A composite expandable medical balloon, the composite expandable medical balloon comprising:
   a base balloon comprising at least one layer of an elastomeric polymer, the base balloon comprising a distal waist portion, a distal cone portion, a body portion, a proximal cone portion, and a proximal waist portion;

an intermediate layer comprising a polymer material; and a fiber braid disposed along the base balloon, the fiber braid comprising at least one polymeric fiber disposed over the base balloon;

wherein the polymer material of the intermediate layer promotes adhesion between the base balloon and the fiber braid;

wherein the base balloon has a first length prior to heat sterilization of the composite expandable medical balloon, the first length being defined between a distal end of the distal waist portion and a proximal end of the proximal waist portion;

wherein the base balloon is designed to have a second length after heat sterilization of the composite expandable medical balloon, the second length being defined between the distal end of the distal waist portion and the proximal end of the proximal waist portion; and wherein the second length is at least 97% of the first length.

2. The composite expandable medical balloon of claim 1, wherein the at least one layer of an elastomeric polymer comprises a polyether-block-amide block copolymer.

3. The composite expandable medical balloon of claim 1, wherein the at least one polymeric fiber comprises an aromatic polyester liquid crystal polymer fiber.

4. The composite expandable medical balloon of claim 1, wherein the at least one polymeric fiber comprises an aromatic polyamide copolymer fiber.

5. The composite expandable medical balloon of claim 1, wherein the at least one polymeric fiber comprises an ultra high molecular weight polyethylene fiber.

6. The composite expandable medical balloon claim 1, wherein the intermediate layer comprises a thermoplastic polymer.

7. The composite expandable medical balloon of claim 6, wherein the intermediate layer comprises a thermoplastic polyurethane.

8. The composite expandable medical balloon of claim 6, further comprising at least one additional layer, the at least one additional layer comprising a thermoplastic polymer, the at least one additional layer being disposed along an outer surface of the fiber braid.

9. The composite expandable medical balloon of claim 8, wherein the at least one additional layer comprises a thermoplastic polyurethane.

10. The composite expandable medical balloon of claim 9, wherein the base balloon has a first diameter prior to heat sterilization of the composite expandable medical balloon;

wherein the base balloon has a second diameter after heat sterilization of the composite expandable medical balloon; and wherein the second diameter is at least 97% of the first diameter.

11. A composite expandable medical balloon, the composite expandable medical balloon comprising:

a heat set base balloon comprising at least one layer of an elastomeric polymer material, the heat set base balloon comprising a distal waist portion, a distal cone portion, a body portion, a proximal cone portion, and a proximal waist portion;

wherein the heat set base balloon has a first length defined by a distal end of the distal waist portion and a proximal end of the proximal waist portion;

an intermediate layer comprising a polymer material; and a fiber braid comprising at least one polymeric fiber disposed over the heat set base balloon;

wherein the polymer material of the intermediate layer promotes adhesion between the base balloon and the fiber braid; and wherein the heat set base balloon is designed to reduce delamination and tenting of the fiber braid from the base balloon during heat sterilization, after heat sterilization, or both; and wherein the heat set base balloon exhibits about 6% less axial and/or radial shrinkage than a non-heat set base balloon.

12. The composite expandable medical balloon of claim 11, wherein the at least one intermediate layer is a thermoplastic material; and further comprising at least one second intermediate layer, the at least one second intermediate layer comprising a thermoplastic polymer material.

13. The composite expandable medical balloon of claim 12, wherein the heat set base balloon comprises a polyether-block-amide block copolymer, the fiber braid comprises an aromatic liquid crystal polymer and the at least one intermediate layer comprises a thermoplastic polyurethane.

* * * * *